United States Patent [19]

Jakkula

[11] Patent Number: 4,607,212
[45] Date of Patent: Aug. 19, 1986

[54] METHOD AND APPARATUS FOR DETECTION OF KNOTS OR THE LIKE IN SAWN LUMBER

[75] Inventor: Pekka Jakkula, Helsinki, Finland

[73] Assignee: A.Ahlstrom Osakeyhtio, Noormarkku, Finland

[21] Appl. No.: 529,619

[22] Filed: Sep. 6, 1983

[30] Foreign Application Priority Data

Sep. 10, 1982 [FI] Finland .................................. 823151

[51] Int. Cl.⁴ ........................................... G01R 27/04
[52] U.S. Cl. ............................................. 324/58.5 R
[58] Field of Search ..................... 324/58.5 R, 58.5 B, 324/58.5 A

[56] References Cited

U.S. PATENT DOCUMENTS 4,123,702 10/1978 Kinanen et al. ................ 324/58.5 A
4,123,703 10/1978 Robinson ........................ 324/58.5 B
4,492,915 1/1985 Caspers ........................... 324/58.5 R

FOREIGN PATENT DOCUMENTS 0139028 12/1979 German Democratic Rep. .................................. 324/58.5 B
2027898 3/1983 United Kingdom .
0211856 11/1968 U.S.S.R. .......................... 324/58.5 B
0244438 3/1970 U.S.S.R. .......................... 324/58.5 A
0293208 12/1971 U.S.S.R. .......................... 324/58.5 A Primary Examiner—Stanley T. Krawczewicz
Attorney, Agent, or Firm—Bucknam and Archer

[57] ABSTRACT

A method and an apparatus for detection of knots in lumber by means of microwave radiation. Radiation from a transmitter is directed toward a piece of lumber and the radiation reflected from and/or passed through the piece of lumber is detected by means of a receiver. A radiation field having a TEM wave mode is established on the surface of the piece of lumber by means of a transmitter, whereby a radiation field which includes a TM wave mode component is generated in a knot in the piece of lumber and this is detected by means of a receiver.

9 Claims, 5 Drawing Figures

METHOD AND APPARATUS FOR DETECTION OF KNOTS OR THE LIKE IN SAWN LUMBER

FIELD OF INVENTION

The invention relates to a method for detection of knots or the like in lumber, especially in sawn goods, by means of radio-frequency electromagnetic radiation, preferably in the microwave range, in which method radiation from one or more transmitters is directed towards a piece of lumber and the radiation reflected from or passed through the piece of lumber is detected by means of one or more receivers.

The factors affecting the quality of timber and sawn goods in particular are knots, discoloration, rot, roughness, small cavities and cracks. The most important property affecting the quality of sawn goods is knottiness; according to some estimates it determines up to 85% of the quality of sawn goods.

DESCRIPTION OF PRIOR ART

Known methods for detecting and measuring knottiness in lumber are visual inspection, optical methods—i.e. methods such as photography, carried out by means of light, and methods based on the use of radio-frequency electromagnetic radiation. Naturally only the latter of methods can be applied in automatical quality grading of lumber.

Known methods utilizing radio-frequency radiation, especially microwave radiation, are based on the fact that changes occur both in the radiation passing through the lumber and the radiation reflected therefrom when a knot or a similar non-homogenity occurs in the radiation field. The changes are either changes in the amplitude or the phase of the radiation field. These changes are compared with the radiation passing through knot-free wood and when there is an abrupt change in the radiation, it is considered to be caused by a knot.

The greatest disadvantage in the known methods utilizing radiation for detecting knots or the like in lumber is the fact that they are not reliable when grading wet wood. Changes in the humidity may be mistaken for knots or the radiation field may be greatly dampened due to humidity.

British patent No. 2027898 B discloses a method for detecting deviant grain direction in timber by means of radio-frequency radiation, especially microwave radiation, utilizing the change in the polarization plane of the transmitted high frequency radio wave energy in anisotropic wood. By means of apparatuses based on this method knots can be detected only when deviation in grain direction is connected to the knots. This method can not be applied to reliable detection of knots.

SUMMARY OF THE INVENTION

It is an object of this invention to eliminate the aforementioned disadvantages and to provide a reliable method and apparatus for detecting knots or similar abrupt changes of the dielectric properties in lumber, preferably sawn goods. As far as the method is concerned, this is accomplished by means of the characteristic features of the invention described in the claims.

One of the advantages of the invention is that the detection of knots is reliable both in dry and wet pieces of lumber. Furthermore, knots can be identified also in the wane part of a piece of lumber, which has not been possible by means of the known methods. It is also possible to determine the ends of a piece of lumber and utilize this e.g. in length measuring.

The apparatus according to the invention is simple as regards the transmitter and the receiver. The apparatus is not susceptible to disturbances and its maintenance is easy, which properties are of primary importance e.g. in the exacting conditions of a saw mill.

BRIEF DESCRIPTION OF THE DRAWINGS

The invention will be described more in detail in the following with reference to the accompanying drawings. In the drawings.

DESCRIPTION OF PREFERRED EMBODIMENTS

Figure 1:
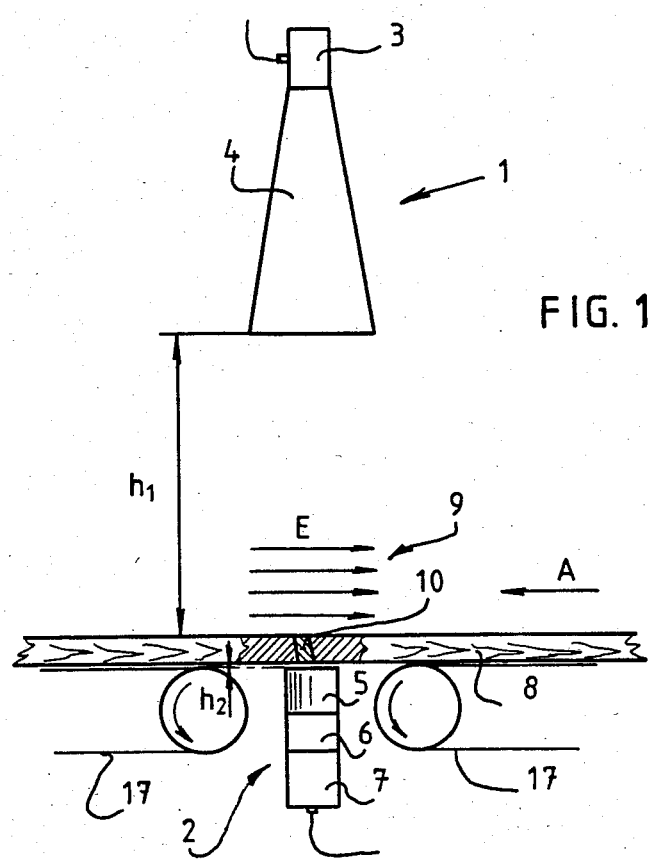
FIG. 1 is a schematic side view of an apparatus according to the invention, in which the radiation field passes through a piece of lumber.

A preferred embodiment of the invention is illustrated in FIG. 1. The apparatus comprises a transmitter 1 and a receiver 2, between which the piece of lumber being examined, such as a board 8, is being transferred longitudinally by means of a conveyor 17. The transmitter 1 consists of a microwave transmitter 3 and a transmitting antenna 4 combined thereto. The receiver 2 consists of a round waveguide 5, a detector 6 and a pre-amplifier part 7.

Microwave radiation which, when reaching the surface of the board, consists of pure TEM-wave mode is fed from the transmitter 1 preferably perpendicularly to the surface of a board 8. It is known that a radiation field having a TEM wave mode does not have a component in its direction of propagation, i.e. no longitudinal electric or magnetic field component. Such a situation is achieved e.g. by generating radiation in a microwave transmitter 3, which radiation has a $TE_{10}$ wave mode, and by feeding this to a horn antenna dimensioned for a corresponding wave mode and acting as a transmitter antenna 4. The transmitter antenna 4 is disposed at a suitable, relatively long distance $h_1$, such as 0.5 m, from the surface of the board so that other wave modes of the radiation field except the pure TEM wavemode 9 have time to be decayed.

A knot 10 in the board 8 is thicker than the rest of the wood material and its dielectricity constant differs from the dielectricity constant of the rest of the wood. Thus the knot causes a dielectric wave guide which goes through the wood. The knot causes a disturbance in the TEM wave mode of the incoming radiation field and new wave modes generate in the knot.

Figure 2:
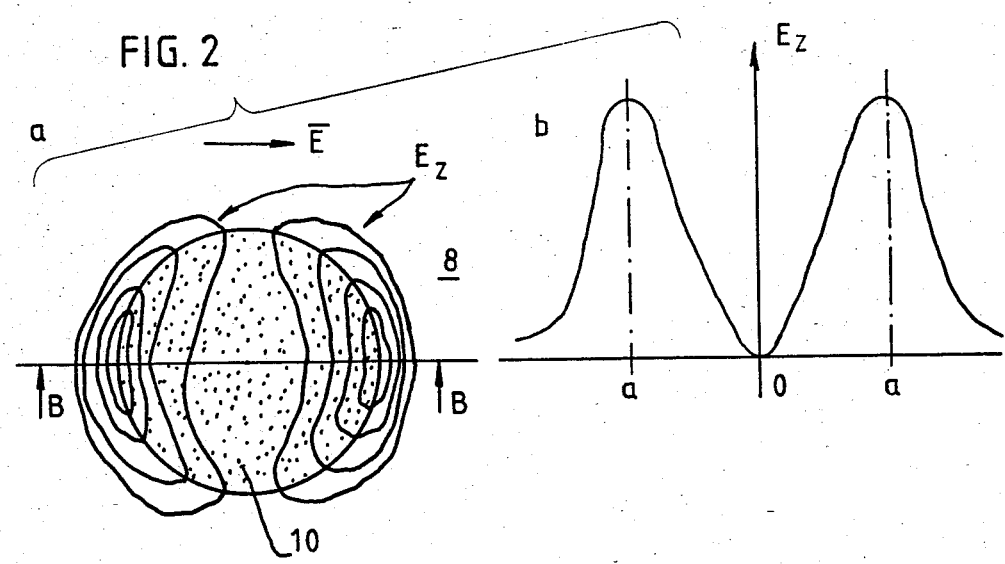
FIG. 2 shows the longitudinal division of the electric field of a radiation field advancing the knot and having a $HE_{11}$ wave mode.

The lowest wave mode advancing in the knot is a $HE_{11}$ mode. The distribution of its longitudinal electric field is shown in FIG. 2. In FIG. 2a the distribution $E_z$ is shown from above in the direction of incidence of a radiation field 9 and in FIG. 2b along the measuring line B—B.

FIG. 2 shows that the radiation field has two tops and is concentrated to a knot's edges with a diameter $2a$.

This has also been proved in measurements. Higher wave modes than $HE_{11}$ can be caused by greater knots in which case the distribution of the electric field has more tops. The tops with the highest amplitudes are, however, in the border surfaces between the knot and the rest of the wood.

$HE_{11}$ wave mode advancing in the knot does not have a lower limiting frequency. This in turn causes a radiation field having such a wave mode theoretically advance even in a very small knot. In practise the decaying of the signal does set the limits to the size of a detectable knot.

Thus in a dielectric waveguide the $HE_{11}$ wave mode is the lowest propagating wave mode of the radiation field. This is a so called mixed mode in which the predominant wave mode is the TM mode. This includes an electric field component in the direction of propogation of the field, as is shown in FIG. 2b.

With regard to the transmitter 1, in the opposite side of the board 8 adjacent its surface and somewhat below the level of a conveyor 17 there is disposed the round waveguide 5 which is dimensioned for the $TM_{01}$ wave mode. The end of the TM-waveguide 5 is open and in its other end there is a detector means 6 correspondingly dimensioned for the $TM_{01}$ mode.

The mouth of the waveguide 5 has to be a relatively short distance $h_2$, such as 0 to 10 mm, from the surface of the board in order to have the $HE_{11}$ mode be properly connected to the waveguide dimensioned for the $TM_{01}$ mode, as the $HE_{11}$ decays mode rapidly in an open space.

In case there are no knots in the part of the board moving in the radiation field between the transmitter and the receiver, no signal is obtained from the detector as the TEM wave coming to the receiver element generates there a $TE_{11}$ wave mode which is reflected from the detector means construed for a $TM_{01}$ mode.

Knots in the eventual wane part of the board can also be detected by means of the method according to the invention. In this case it is advantageous to direct toward the board to be examined a radiation field having a TEM wave mode the polarisation of which, i.e. the direction of the electric field component, is parallel to the longitudinal axis of the board. Thus no strong signal is obtained from the wane, as is the case when using polarisation transverse to the board. This is caused by the fact that an axial electric field component is formed when the incoming radiation field is deflected from an inclined surface in the wane of the board.

Figure 3:
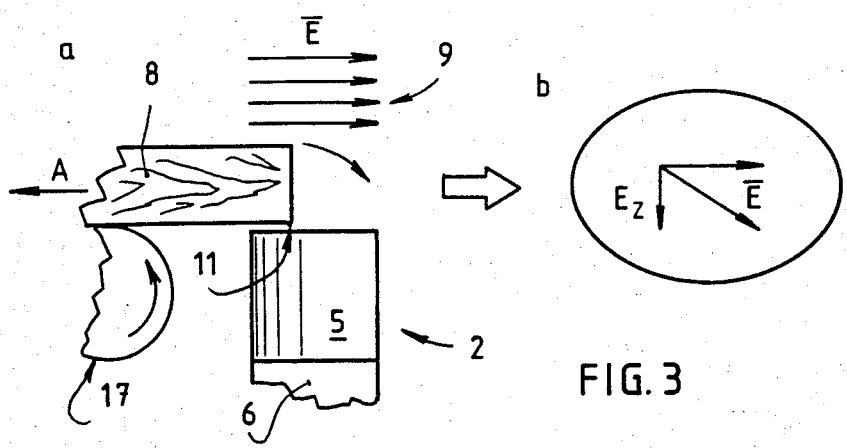
FIG. 3 is a schematic side view of the detection of the end of a piece of lumber.

The boundary surface between two dielectric materials in front of the mouth of a wave guide 5 of the receiver 2 also causes a strong signal to the detector, in case the boundary surface is asymmetrical with regard to the electric field component $\overline{E}$, i.e. the polarization direction of the incoming TEM wave mode. This is caused, as is illustrated in FIGS. 3a and 3b, by the fact that the polarization direction of the incoming TEM wave mode 9 turns at the boundary surface 11 into a longitudinal polarization $E_2$ which adjacent to the mouth of the wave guide of the receiver generates a TM wave mode including a longitudinal electric field. This phenomenon can be utilized in identifying the end of a board. In this way also a crack or a hole from which e.g. a dead knot has loosened, can be detected.

Figure 4:
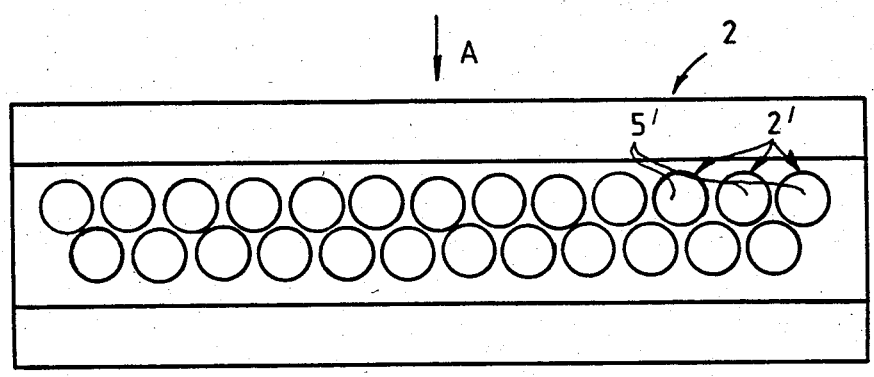
FIG. 4 illustrates a receiver structure.

A desired number of receivers 2' can be disposed in a line adjacent each other. The board to be examined is transferred longitudinally in the direction A by means of a conveyor perpendicularly against the receiver line through the transmitter and the receiver. The receivers are read successively swiftly and the obtained data is fed to a data processing unit. In this way it is possible to examine the knottiness of the board in its entire width. The receivers 5' are preferably disposed zigzagged in two rows so that they tangent to each other's measuring line, as is illustrated in FIG. 4. Thus not even a small knot is able to pass between individual receivers 5' without being noticed, when the board is moved in the direction A.

The wave guides 5, 5' of the receivers 2 are preferably casted full of plastics. Thus the detectors 6 are efficiently protected.

The receiver element 5, 5' can be substituted by some detector sensitive to a longitudinal polarization field. In practice it has been found, however, that a detector of this kind is, irrespective of its type, considerably more susceptible to disturbances than the above presented combination of a wave guide dimensioned for the TM wave mode and a corresponding detector.

Figure 5:
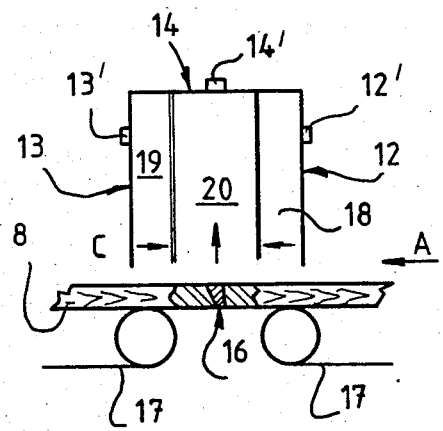
FIG. 5 is a schematic view, partly in section, of another apparatus according to the invention, in which the radiation field is reflected from a piece of lumber.

Another embodiment of the invention is illustrated schematically in FIG. 5. A transmitter 12, 13 and a receiver 14 are disposed on the same side of the piece of lumber 8 to be examined which is transferred longitudinally along a conveyor 17 past the measuring point where the radiation reflected from knots 16 is measured.

The receiver consists preferably of a pair of transmitters 12 and 13 connected balanced to each other with a phase shift of 180° between them, whereby variations in the distance of the lumber from the transmitter-receiver do not affect the measurement results, as in the case in a measurement arrangement with one transmitter-receiver pair. Both transmitters consist of microwave transmitters 12', 13' which generate radiation having a TE wave mode to transmitter antennae 18, 19. A receiver 14 comprising a wave guide 20 dimensioned for the TM wave mode and a detector 14' are disposed between the transmitters. Arrows C illustrate the polarization directions of the fields.

In principle the apparatus according to FIG. 5 operates in the same way as the knot detector illustrated in FIG. 1 based on the passing through of the radiation. The transmitter field which has a pure TEM wave mode when entering the surface of the board, generates in a knot a TM wave mode which is detected by means of a receiver 14.

While two specific embodiments of the invention have been described in detail above, it is to be understood that various modifications may be made from the specific details described without departing from the spirit and scope of the invention. Thus e.g. many transmitters can be used as well as many receivers.

What is claimed is:

1. A method for detecting knots in a piece of lumber, sawn goods and the like, which consist of generating electromagnetic radiation in the microwave range, directing said electromagnetic radiation onto one surface of said piece of lumber by means of at least one transmitter at such a distance from the lumber that the radiation field on the surface of said piece of lumber consists of TEM wave mode alone, generating a radiation field having a TM wave mode component in a knot in said piece of lumber, passing said radiation through said lumber and detecting said TM wave mode component by at least one receiver comprising a round wave guide combined with a detector dimensioned for the TM wave mode.

2. The method according to claim 1 wherein said electromagnetic radiation is directed onto one surface of said piece of lumber perpendicularly to the direction of travel of said piece of lumber, the radiation is passed through said lumber and said TM wave mode component is detected on the side opposite to said one surface and adjacent to the other surface.

3. A method for detecting knots in a piece of lumber, sawn goods and the like, which consists of generating electromagnetic radiation in the microwave range, directing said electromagnetic radiation onto one surface of said piece of lumber by means of at least one transmitter at such a distance from the lumber that the radiation field on the surface of said piece of lumber consists of TEM wave mode alone, generating a radiation field having a TM wave mode component in a knot in said piece of lumber, reflecting said radiation from said piece of lumber and detecting said TM wave mode component by at least one receiver comprising a round wave guide combined with a detector dimensioned for the TM wave mode.

4. The method according to claim 3 wherein said TM wave mode is detected on the same side the radiation is directed onto the piece of lumber.

5. An apparatus for detecting knots in lumber, sawn goods and the like by means of electromagnetic radiation in the microwave range which comprises at least one transmitter (1: 12, 13) and a transmitter antenna (4: 18, 19) and at least one receiver (2: 2': 14) formed of a receiver antenna (5: 5': 20) and a detector (6: 14'), means for conveying said piece of lumber perpendicularly to said electromagnetic radiation, said transmitter antenna being a horn antenna dimensioned for the TEM wave mode and disposed at a considerable distance (H1) from the surface of the piece of lumber, whereby the radiation field on the surface of said piece of lumber consists of TEM wave mode alone and the receiver antenna is a round wave guide (5: 5':20) dimensioned for the TM wave mode, the detector (6: 14) is adjusted for the TM wave mode.

6. The apparatus according to claim 5 wherein said round wave guide is disposed on the side opposite to the side where said radiation is directed onto the piece of lumber.

7. The apparatus according to claim 5 wherein said round wave guide is disposed on the same side where said radiation is directed onto the piece of lumber, the apparatus comprises at least one pair of transmitters (12, 13), said transmitters being balancedly connected to each other with a phase difference of 180 degrees, and at least one receiver (14) is disposed between said pair of transmitters, whereby they form a transmitter receiver unit.

8. The apparatus according to claim 5 wherein the receiver (2) consists of single receivers (2') disposed zigzagged in two rows.

9. An apparatus according to claim 5 wherein the wave guide of the receivers is filled with plastic material.

* * * * *